United States Patent [19]

Lewis et al.

[11] 4,435,602

[45] Mar. 6, 1984

[54] CONVERSION OF DIMETHYL ETHER TO FORMALDEHYDE

[75] Inventors: Robert M. Lewis, Sugarland; Lynn H. Slaugh, Cypress, both of Tex.

[73] Assignee: Shell Oil Company, Houston, Tex.

[21] Appl. No.: 402,017

[22] Filed: Jul. 26, 1982

[51] Int. Cl.$^3$ ............................................ C07C 47/04
[52] U.S. Cl. .................................................. 568/470
[58] Field of Search ................................ 568/470, 496

[56] References Cited

U.S. PATENT DOCUMENTS 2,467,223  4/1949  Payne .................................. 568/470
3,655,771  4/1972  Tadenuma .......................... 568/470

FOREIGN PATENT DOCUMENTS 1254359  11/1967  Fed. Rep. of Germany ...... 568/470
 413139   7/1974  U.S.S.R. ............................. 568/470
 294465  11/1977  U.S.S.R. ............................. 568/470

Primary Examiner—Werren B. Lone

[57] ABSTRACT

A process is disclosed for oxidizing dimethyl ether to formaldehyde using naturally occurring manganese nodules as a catalyst.

6 Claims, 2 Drawing Figures

CONVERSION OF DIMETHYL ETHER TO FORMALDEHYDE

FIELD OF THE INVENTION

This invention relates to a process for converting dimethyl ether to formaldehyde utilizing as a catalyst naturally occurring manganese nodules.

BACKGROUND OF THE INVENTION

Manganese nodules have been found on both ocean floors and in fresh water. These nodules have been noted as a valuable mineral resource of the future. Many investigations have been made on the mining of these nodules and the extraction of valuable minerals therefrom. These manganese nodules generally certain 30 kinds of metals or more, in the form of oxides or hydroxides. The principal metallic components are primarily manganese and iron, although silicas are present in significant amounts. Manganese nodules have been found suitable for use as oxidation catalysts in converting carbon monoxide to carbon dioxide. (P. B. Weisz, *Journal of Catalysis*, 10, 407-408 (1968)). They have been utilized as catalysts for the decomposition of isopropyl alcohol (Matsuo et al, *Journal of Catalysis*, 54, 446-449 (1978)). In this reference isopropyl alcohol is converted to acetone, carbon dioxide and water. Chang et al (*Ind. Eng. Chem., Process Des. Dev.*, Vol. 15, No. 1, 166-164 (1976)) illustrates a use of manganese nodules for the demetalation of petroleum residues. Manganese nodules have also been noted to carry out the reduction of nitric oxide with ammonia (Wuu et al, *Atmos. Environ.*, 6, 303 (1972)).

Formaldehyde is a chemical used extensively as a reagent, preservative, embalming agent, antiseptic and deodorant and industrially, in large quantities in the synthesis of many substances such as plastics. A process that would convert a readily available syngas chemical such as dimethyl ether to a more valuable substance like formaldehyde could be of commercial interest. Known commercial catalysts for converting dimethyl ether to formaldehyde are stannic phosphate (V. D. Mezhov, M. M. Levkovich & G. M. Sychera, U.S.S.R. Pat. No. 294465, "Method of Production of Formaldehyde", Nov. 1, 1977) and tungstic acid (H. Tadenuma, T. Murakami and H. Mitsushima, U.S. Pat. No. 3,655,771, "Process for Producing Formaldehyde", Apr. 11, 1972).

SUMMARY OF THE INVENTION

The instant invention comprises a process for oxidizing dimethyl ether to formaldehyde by contacting dimethyl ether and oxygen with a catalyst which comprises naturally occurring manganese nodules. These nodules typically contain from about 5 to about 40 percent by weight of manganese and from about 1 to about 40 percent by iron in the form of an oxide or a hydroxide thereof. The use of these manganese nodules provides for a significant yield of formaldehyde from dimethyl ether. These manganese nodules are readily available, comparatively inexpensive and provide an ease of use not exhibited by other commercial catalysts.

DESCRIPTION OF THE PREFERRED EMBODIMENTS

Figure 1:
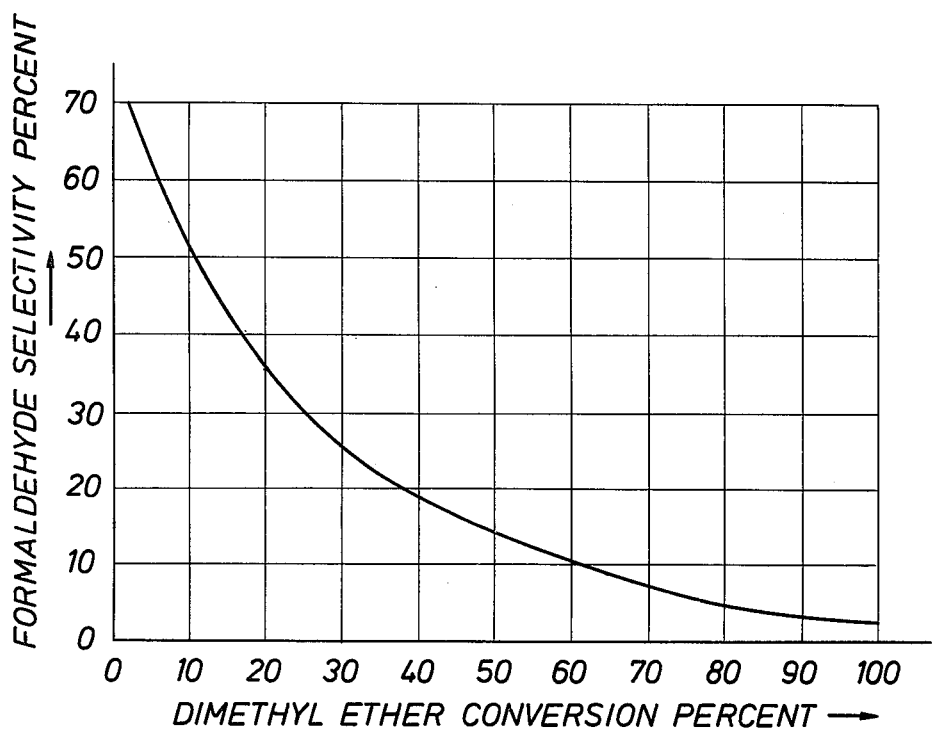
FIG. 1 shows the formaldehyde selectivity as a function of dimethyl ether conversion when using manganese nodules to oxidize dimethyl ether to formaldehyde.

The manganese nodules utilized as catalysts in the instant process are those naturally occurring manganese nodules that are found on ocean floors and in fresh water. They comprise primarily oxides and hydroxides of the manganese and iron with silica present in lesser amounts and with various transition metal and rare earth metal oxides and hydroxides also present in small amounts. Typically, the catalysts useful in the instant process will contain from about 5 to about 40 percent by weight of manganese (measured as a metal) and from about 1 to about 40 percent by weight of iron (measured as a metal). Smaller amounts of silica present in these modules can range up to 30 percent by weight. The silica is essentially inert in the process of the instant invention and can be considered as acting as an inert support for the active metals, such as iron and manganese. The manganese nodules useful as catalysts have relatively high surface areas. Typically surface areas will range from about 100 to about 300 $m^2/gm$, preferrably from about 150 to about 250 $m^2/gm$. Table 1, taken from Chang et al, *Ind. Eng. Chem., Process Des. Develop.*, Vol. 13, No. 3, 315-316 (1974) illustrates typical properties and metal analyses of nodules which would be suitable as catalysts in the instant process and which were taken from the Pacific Ocean, the Atlantic Ocean and Lake Michigan.

TABLE 1
TYPICAL PROPERTIES OF MANGANESE NODULES

| Nodule Source | Pacific Ocean | Atlantic Ocean | Lake Michigan |
|---|---|---|---|
| Surface area, $m^2/g$ | 230 | 226 | 233 |
| Particle density, $g/cm^2$ | 1.52 | 1.43 | 1.49 |
| Average pore diameter, A | 69 | 73 | 81 |
| Pore volume, $cm^3/g$ | 0.40 | 0.41 | 0.41 |
| Real density, $g/cm^3$ | 3.80 | 3.53 | 3.75 |
| Metals analysis | wt. % | | |
| Mn | 28.5 | 18.8 | 9.2 |
| Fe | 13.9 | 12.3 | 35.4 |
| Ni | 1.21 | 0.72 | 0.01 |
| CoO | 0.23 | 0.46 | 0.04 |
| $MoO_2$ | 0.1 | 0.10 | 0.08 |

The manganese nodules are used in a fashion typical of that used for heterogeneous catalysts. They may be used in fixed beds, and fluidized beds or in reactors. Typical reaction temperatures range from about 250° C. to about 500° C. Typical reaction pressures range from atmospheric to about 500 bars, preferably from atmospheric to about 200 bars. Typical feed rates include gaseous hourly space velocities ranging from about 500 to about 25,000 l/l/hr.

The formaldehyde is prepared by oxidizing the dimethyl ether with oxygen. Generally, the oxygen is provided diluted with an inert gas such as nitrogen. Air provides a suitable oxygen-containing feed gas. Suitable precautions should be taken to avoid the hazards of explosive oxyyen-hydrocarbon mixtures.

The manganese nodules may be utilized in the form in which they are mined. For example, they may be loaded into a tubular reactor in the nodule form. In many cases, however, it is desirable to crush and sieve the nodules to certain selected size ranges.

The process of the instant invention is further described below by the following illustrative embodiments which are provided for illustration and are not to be construed as limiting the invention.

ILLUSTRATIVE EMBODIMENTS

Manganese nodules were obtained from Kennecott Copper Company and their physical and chemical properties were analyzed. These properties are illustrated in Table II below.

TABLE II
PROPERTIES OF NODULES OBTAINED FROM KENNECOTT

| Analysis (wt %) | |
|---|---|
| | 36.1 Mn |
| | 0.4 Ba |
| | 6.7 Si |
| | 0.9 K |
| | 3.7 Fe |
| | 44.0 O |
| | 1.0 Ca |
| | 1.0 Ti |
| Trace amounts of | Ni, Cu, Zn, La, Ce, Sr, Y, Rb, Pb, Sb, Zr, Co |
| Surface Area | 168 m$^2$/gm |
| Pore Volume | .612 cc/gm |

The manganese nodules, as received, were ground and sieved to 20-30 mesh particle size. The particles were loaded into a quartz tube and were tested in a flow reactor isolated in a barricade cell. The reactor was operated at atmospheric pressure with a volume concentration of dimethyl ether in air of 4.6-5.5%. The results for a series of runs in which the reactor temperature and catalyst volume (hence gas hourly space velocity) were varied are tabulated in FIG. 2.

FIGURE 2

| Run | Gas Hourly Space Velocity | Reactor Temp. (°C.) | Dimethyl Ether Conversion (%) | Formaldehyde Selectivity (%) | Formaldehyde Yield (%) |
|---|---|---|---|---|---|
| 1* | 4000 | 450 | 37 | 0 | 0 |
| 2* | 7600 | 450 | 92 | 0 | 0 |
| 3 | 16000 | 450 | 17 | 37 | 6 |
| 4 | 16000 | 400 | 13 | 38 | 5 |
| 5 | 16000 | 350 | 18 | 49 | 9 |
| 6 | 8000 | 300 | 6 | 69 | 4 |
| 7 | 8000 | 350 | 21 | 38 | 8 |
| 8 | 5300 | 350 | 86 | 3 | 2 |

*100% selectivity to carbon dioxide.

Figure 2:
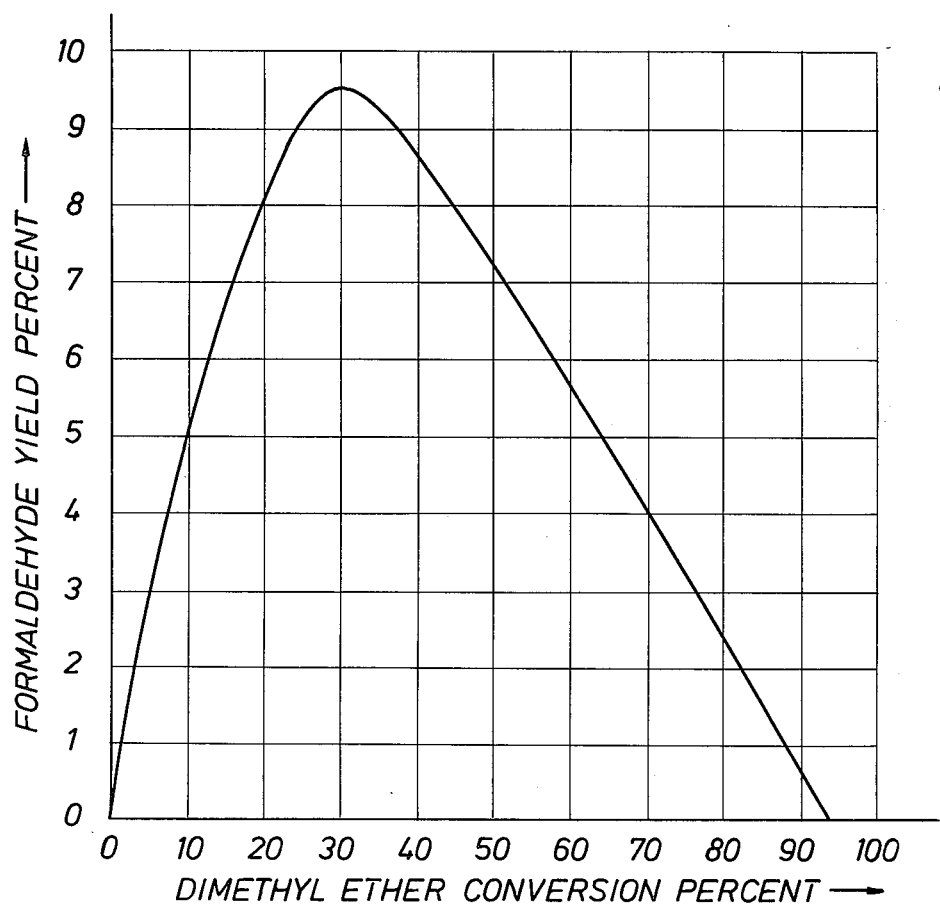
FIG. 2 shows the formaldehyde yield as a function of dimethyl ether conversion when using manganese nodules to oxidize dimethyl ether to formaldehyde.

The above results for formaldehyde selectivity and yield are plotted in FIG. 1 and FIG. 2. The data from run 1 was inexplicably inconsistent with the rest of the data and was omitted. As demonstrated by FIG. 1, the catalyst is more selective for formaldehyde production at lower dimethyl ether conversion. From FIG. 2, it can be seen that the maximum formaldehyde yield using these particular manganese nodules will be about 10% at conversions of less than about 30%.

We claim:

1. A process for converting dimethyl ether to formaldehyde which comprises contacting the dimethyl ether with oxygen at a temperature ranging from about 250° C. to about 500° C. with a catalyst comprising naturally occurring manganese nodules.

2. The process of claim 1 wherein the manganese nodules contain from about 5 to about 40 percent by weight of manganese and from about 1 to about 40 percent by weight of iron.

3. The process of claim 1 wherein the manganese nodules have a surface area ranging from about 100 to about 300 m$^2$/gm.

4. The process of claim 3 wherein the surface area ranges from about 150 to about 250 m$^2$/gm.

5. The process of claim 1 wherein the pressure ranges from atmospheric to about 500 bar.

6. The process of claim 1 wherein the gaseous hourly space velocity ranges from about 500 to about 25,000 l/l/hr.

* * * * *